United States Patent [19]

Sharma

[11] Patent Number: 5,406,085
[45] Date of Patent: Apr. 11, 1995

[54] APPARATUS AND METHOD FOR RAPID AND NONDESTRUCTIVE DETERMINATION OF LATTICE DEFECTS IN SEMICONDUCTOR MATERIALS

[75] Inventor: Suresh C. Sharma, Arlington, Tex.

[73] Assignee: Board of Regents, The University of Texas System, Austin, Tex.

[21] Appl. No.: 88,482

[22] Filed: Jul. 7, 1993

[51] Int. Cl.[6] .................... G01N 23/00; G01N 23/18
[52] U.S. Cl. .................................. 250/358.1; 250/308
[58] Field of Search ....................... 250/358.1, 308, 309

[56] References Cited

U.S. PATENT DOCUMENTS

| | | |
|---|---|---|
| 3,593,025 | 7/1971 | Grosskreutz . |
| 3,970,855 | 7/1976 | Holt et al. . |
| 4,064,438 | 12/1977 | Alex et al. .................... 250/358.1 X |
| 4,652,757 | 3/1987 | Carver ......................... 250/358.1 X |
| 4,740,694 | 4/1988 | Nishimura et al. .................. 250/306 |
| 4,864,131 | 9/1989 | Rich et al. . |
| 4,897,549 | 1/1990 | Zerda et al. . |
| 5,077,475 | 12/1991 | Moriya et al. .................. 250/341 X |
| 5,200,619 | 4/1993 | Kumar et al. .................... 250/308 X |

FOREIGN PATENT DOCUMENTS

| | | | |
|---|---|---|---|
| 217028 | 1/1985 | Germany .................... | 250/358.1 |
| 1052955 | 11/1983 | U.S.S.R. .................... | 250/358.1 |

OTHER PUBLICATIONS

S. Dannefaer, "A Systematic Study of Positron Lifetimes in Semiconductors," *J. Phys. C.: Solid State Phys.*, vol. 15, pp. 599–605 (1982).

G. Dlubek and R. Krause, "Positron Studies of Defects in III–V Semiconductor Compounds," *Phys. Stat. Sol.*, vol. 102, pp. 443–479 (1987).

P. Kirkegaard et al., "Program System for Analysing Positron Lifetime Spectra and Angular Correlation Curves," *Computer Physics Communications*, vol. 23, pp. 307–355 (1981).

S. C. Sharma, N. Hozhabri, and R. C. Hyer, "A Study of Defects in Czochralski–Grown Silicon by Positron Annihilation Spectroscopy," 262 *Mat. Res. Soc. Symp. Proc.* pp. 45–50 (1992).

S. C. Sharma et al., "Depth and Radial Profiles of Defects in Czochralski–Grown Silicon," 61 *Appl. Phys. Lett.* pp. 1939–1941 (Oct., 1992).

*Primary Examiner*—Constantine Hannaher
*Assistant Examiner*—Edward J. Glick
*Attorney, Agent, or Firm*—Arnold, White & Durkee

[57] ABSTRACT

A method and apparatus for rapidly yet nondestructively testing a semiconductor wafer is disclosed. A multi-spot positron source assembly directs positrons over an entire semiconductor wafer at one time. A pair of multi-detector assemblies are situated so that each detector within an assembly corresponds physically with a positron source. By measuring the characteristic emission and annihilation energies, the multi-detector assembly pair is capable of detecting the lifetimes of positrons from within each of the areas simultaneously. Longer lifetimes are indicative of defects within the semiconductor wafer. By accumulating and analyzing positron lifetimes from across the entire wafer substantially simultaneously, information about the existence and location of defects in the wafer may be more rapidly determined than is possible with known positron-emission techniques.

16 Claims, 4 Drawing Sheets

APPARATUS AND METHOD FOR RAPID AND NONDESTRUCTIVE DETERMINATION OF LATTICE DEFECTS IN SEMICONDUCTOR MATERIALS

BACKGROUND OF THE INVENTION

1. Field of the Invention

The present invention relates generally to a system for the detection and quantification of lattice defects in semiconductor materials. The invention, more specifically, concerns a method and apparatus for nondestructive determination of lattice defects by the technique of positron lifetime spectroscopy using an array of detectors.

2. Description of Related Art

The technique of positron annihilation is known in the art as a method for nondestructive testing of defects in crystalline structures, as well as for determining metal fatigue. In the basic method a positron is emitted from a radioactive material ($^{22}$Na for example) placed proximate to the specimen material. At approximately the same time, a nuclear gamma ray is emitted, signalling the birth of the positron. This nuclear gamma ray (or "start" ray) has a unique energy of approximately 1.28 MeV. When the positron enters the specimen material, such as a semiconductor wafer, it quickly loses its energy, reaches thermal equilibrium, and seeks out an electron in the material with which it interacts (annihilates). The interaction of positive and negative charges results in complete annihilation of both the positron and electron, and further causes the emission of two (or, rarely, three) gamma rays each having a unique characteristic energy of approximately 0.51 MeV. As a result, the end of the lifetime of an individual positron is signalled by the radiation of a unique energy. Once the time difference between the emission of the 1.28 MeV "start" gamma ray and the 0.51 MeV "stop" gamma rays is known, the time duration of existence of the positron in the material may be determined.

The lifetime of the positron in a material is instructive on the existence of defects in that material because it has been found that the lifetime of positrons is longer in materials containing defects such as vacancies and microvoids. The theory behind the increased positron lifetime is that the positrons become trapped in the voids, thus staying alive for a longer time due to a reduction in the number of available electrons inside the defect. A precise measurement of changes in the lifetime of positrons may reveal much information about the defects present in the sample material.

The foregoing discussion of the positron annihilation technique is by way of background only. Further details may be had by reference to U.S. Pat. No. 3,593,025, entitled "Detecting Defects by Distribution of Positron Lifetimes in Crystalline Materials," issued to Grosskreutz on Jul. 13, 1971, the disclosure of which is herein incorporated by reference. In addition, more information on the theory of positron annihilation spectroscopy may be had by reference to *Positron Solid-State Physics*, edited by W. Brandt and A. Dupasquier, North-Holland, Amsterdam, 1983.

The positron annihilation technique described above is a standard research laboratory technique. It has not yet, however, evolved into an "industrial tool" for quality control of defects in semiconductor materials, for two basic reasons: (1) the data collection and analysis takes too long to be suitable for the quality control of defects in an industrial environment, and (2) the technique has largely been geared toward the study of metallic samples, which are relatively easier to control and understand as compared to semiconductor wafers.

With regard to semiconductor materials specifically, basic laboratory experiments have demonstrated the potential of the positron annihilation technique for the investigation of defects such as vacancies and microvoids. Such information is not, in fact, known to be available from other nondestructive techniques.

From a practical standpoint, knowledge of the purity of a semiconductor material is critical, in that the presence or absence of defects in a semiconductor wafer determines whether a device made from that wafer will meet desired specifications. Due to inherent problems in the growth process of silicon wafers, significant differences may exist in the types and concentrations of defects throughout different wafers from the same ingot, or even throughout a single wafer. Variations in defects within a single wafer could cause electronic chips made from the same wafer to perform very differently. In other words, whereas one device may perform beautifully, another device made from the same wafer may totally fail. Thus, random "spot" testing is not an effective method for accurately predicting the performance of an entire semiconductor wafer. Only knowledge of the vacancy contents (or presence of defects) across an entire wafer will permit industry to accurately predict whether to use an entire wafer, or selected portions, for device fabrication, or whether to discard a defective wafer altogether. Such reliable prediction will greatly reduce the expense associated with defective semiconductor devices and also with wasting acceptable portions of otherwise defective wafers.

In U.S. Pat. No. 4,897,549, Zerda et al. discuss a method of measuring pore diameters by positron decay. In the method described, a radioactive source is sandwiched between two specimens of the sample material and a scintillation counter is disposed on either side of the specimen material. A positron is emitted from the radioactive source and enters the material. Once it enters the material, the positron decays into the characteristic gamma rays described above. Phototubes are provided to detect the characteristic energy emission. Constant fraction differential discriminators are coupled to the phototubes to pass signals corresponding to the prompt gamma ray emission, which in turn pass signals to a time-to-amplitude converter and then to a multichannel analyzer. Each spectrum is measured for 1 to 8 hours to accumulate a sufficient number of pulses. Further discussion of this technique may be had by reference to S. C. Sharma et al., "Depth and Radial Profiles of Defects in Czochralski-grown Silicon," 61 *Appl. Phys. Lett.* pp. 1939-1941 (Oct. 19, 1992).

Using the positron lifetime measurements progressively made across an entire wafer, it is theoretically possible to map lattice defects across the entire wafer. However, the substantial time involved is prohibitive. In the typical method of positron-annihilation testing (such as that described in Zerda et al. and Sharma et al.), the measurement of a lifetime spectrum provides defect information over a spot size of only about 2 to 3 mm$^2$ on a wafer. Each spectrum in turn requires 1 to 8 hours of measurement time. Then, to map the entire surface of a typical 6 to 8 inch semiconductor wafer, the positron source must be manually displaced. Thus, it could take one to two weeks using conventional positron annihilation methods to scan a single semiconductor wafer. This time period would be prohibitively long in the industrial environment, where it is desirable to scan large numbers of wafers almost routinely.

Thus, a need exists for a technique of nondestructively yet rapidly determining semiconductor wafer defects in an industrial environment.

SUMMARY OF THE INVENTION

The problems outlined above are addressed by the device and method of the present invention. The present invention comprises a multi-detector system with a specially designed multi-spot positron source for use in the positron-lifetime technique. The multi-detector assembly comprises a plurality of scintillator detectors arranged so that multiple areas on a semiconductor test wafer may be tested simultaneously. The multi-spot positron source is designed so that each radioactive source spot corresponds physically to a pair of scintillator detectors. In a preferred method of operation, the system is computer controlled, receiving positron lifetime spectral data from a plurality of areas (each corresponding to a pair of detectors/source-spot assembly) of the semiconductor test wafer simultaneously. Thus, by using a sufficient number of detector/source-spot pairs, an entire surface area of a typical semiconductor wafer may be accurately scanned for defects in a commercially feasible period of less than one hour, as opposed to the scan time period of days to a week currently possible in the art. This improvement is possible because of the realization of the simultaneous measurements on a number of spots on the wafer and also by using more efficient scintillation counters (BaF$_2$, as opposed to the usual plastics, for example).

The advantages of the present invention will be further appreciated from the drawings and from the detailed description provided below.

BRIEF DESCRIPTION OF THE DRAWINGS

The herein described advantages and features of the present invention, as well as others which will become apparent, may be attained and understood in more detail by reference to the following description and appended drawings, which form a part of this specification.

It is to be noted, however, that the appended drawings illustrate only exemplary embodiments of the invention and are therefore not to be considered limiting of its scope, for the invention may admit to other equally effective embodiments.

DETAILED DESCRIPTION OF THE PREFERRED EMBODIMENTS

Figure 1:
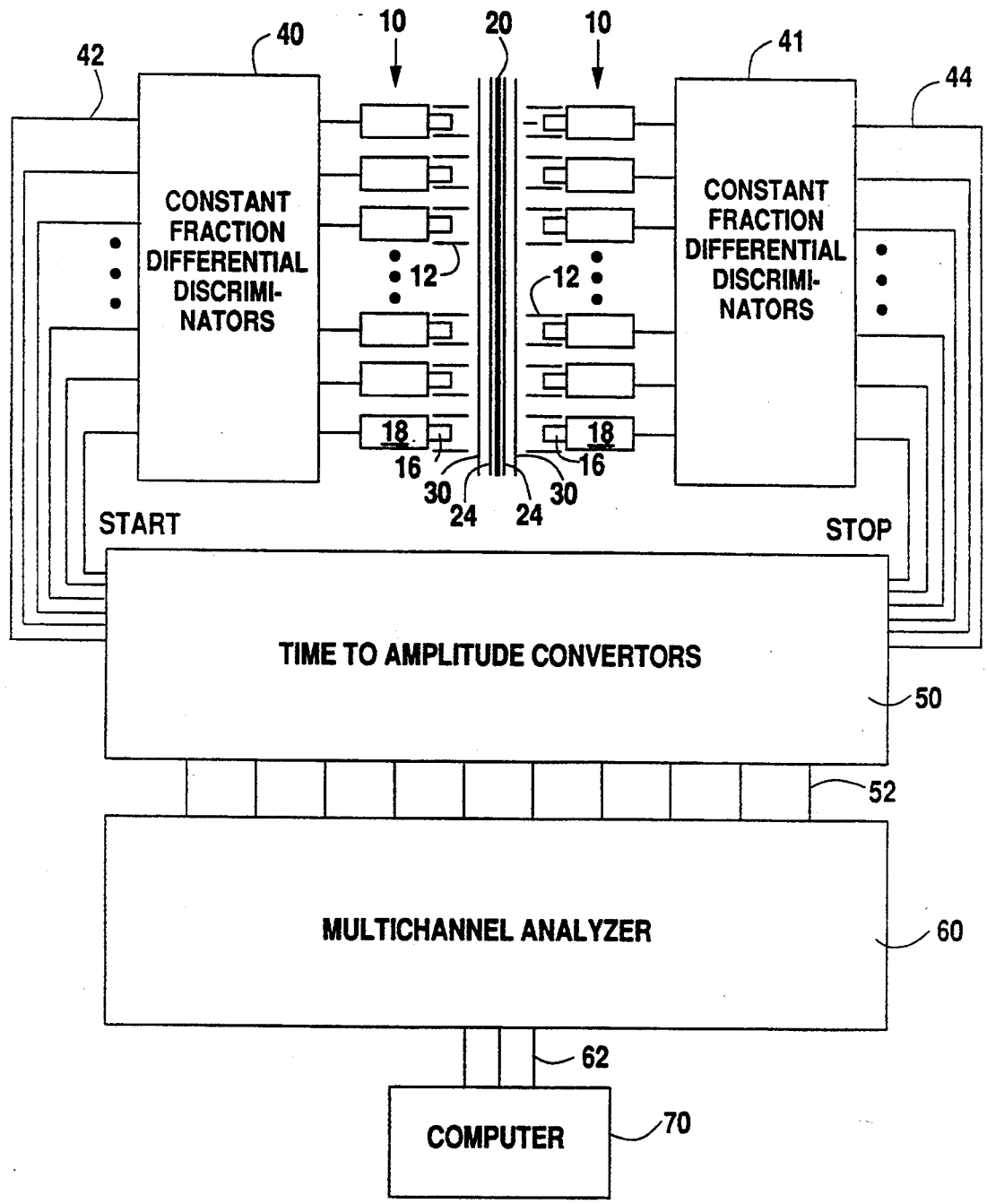
FIG. 1 is a side view of a multi-source, multi-detector positron lifetime spectroscopy testing system in accordance with the present invention.
Figure 2:
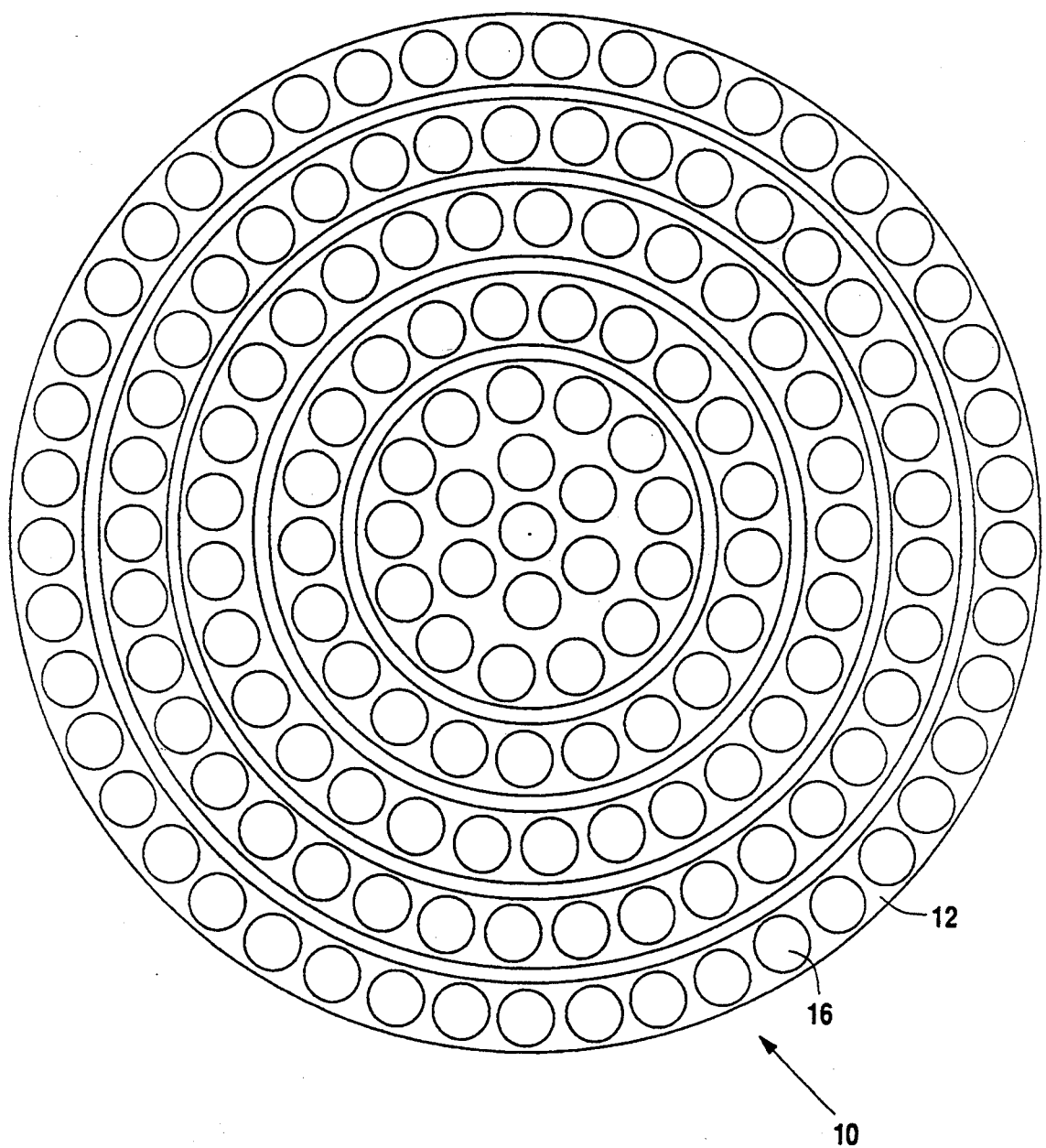
FIG. 2 is a preferred schematic layout of a multi-detector assembly in accordance with the present invention.

Turning now to the drawings, FIG. 1 is a side view of a multi-source, multi-detector positron lifetime spectroscopy testing system in accordance with the present invention. A preferred testing apparatus comprises two multi-detector assemblies 10, shown in more detail in FIG. 2. Each multi-detector assembly 10 is preferably comprised of multiple BaF$_2$ scintillators 16 arranged so as to cover the entire diameter (6 to 8 inches) of a typical semiconductor wafer 30 (FIG. 1). To minimize cross-talk, each scintillator 16 is shielded from the neighboring scintillators 16 by sufficient lead shielding 12 cast into the empty spaces between the scintillators such that each scintillator is completely surrounded by the lead shielding. As shown in FIG. 1, each scintillator 16 is coupled to a suitable photomultiplier tube 18, which is preferably shielded from the earth's magnetic filed by use of appropriate $\mu$-metal shields. It is desirable that the photomultiplier tubes 18 be of the smallest-available diameter, so that a sufficiently large number of these tubes can be accommodated over the test wafer. For example, the Hamamatsu type R2496 Photomultiplier Tube is only $\frac{3}{8}''$ in diameter, and it is suitable for the BaF$_2$ scintillator provided by Bicron.

Figure 3:
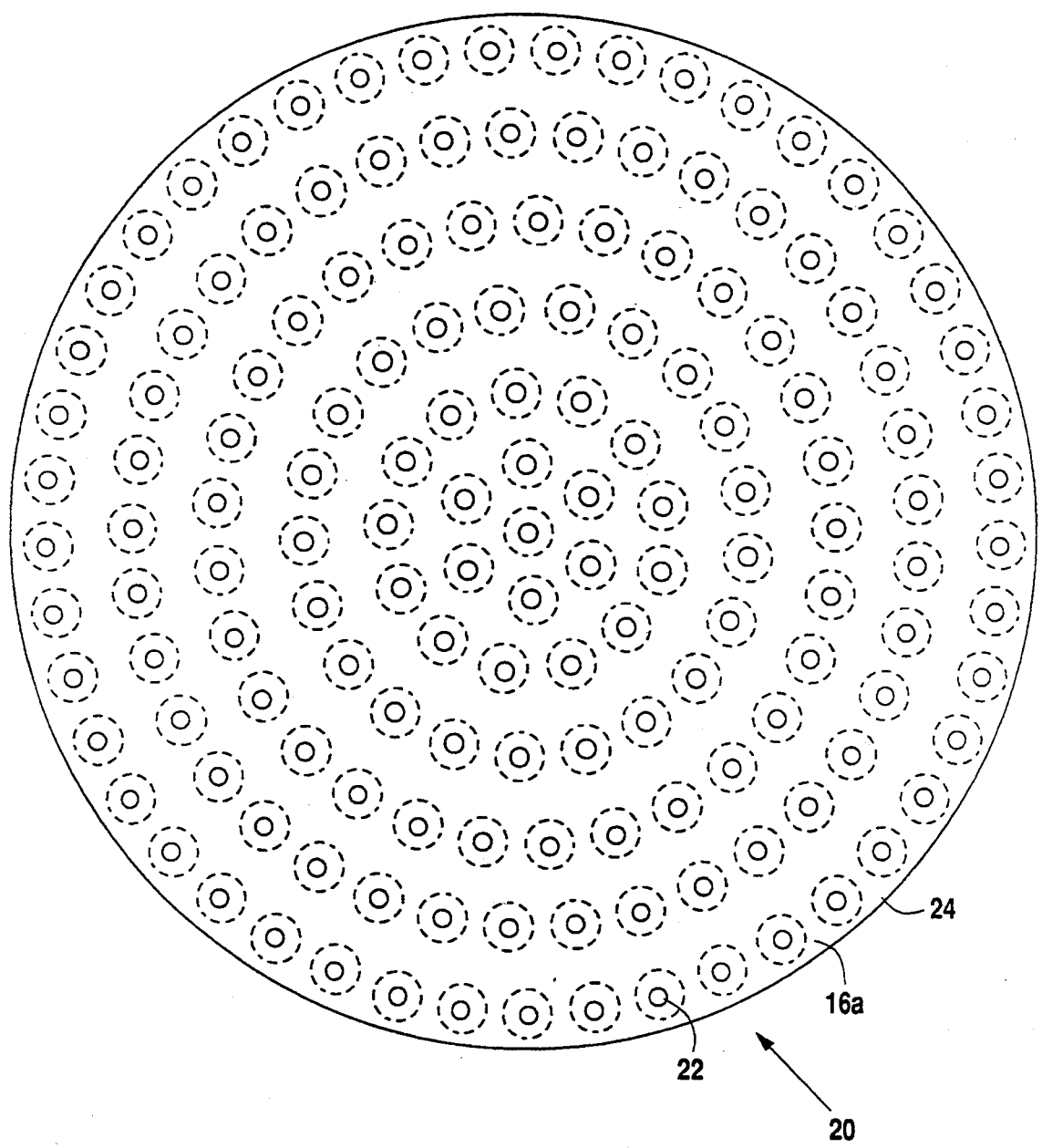
FIG. 3 is a preferred schematic layout of a multi-spot positron source assembly in accordance with the present invention.

The testing apparatus of FIG. 1 is also comprised of a multi-spot positron assembly 20, shown in more detail in FIG. 3. Positron source assembly 20 may be configured in a sandwich arrangement between two pin-hole free foils 24 of a diameter preferably equal to that of the wafer being tested. Such foils 24 are preferably comprised of nickel with a thickness of approximately 1 $\mu$m. Radioactive material (such as $^{22}$NaCl) is preferably deposited in spots 22 of less than approximately 1 mm distributed so as to cover the diameter of the wafer 30 to be tested. Each spot 22 may contain as few as 2 $\mu$Ci of radioactivity. The source foil 24 is covered by another, preferably nickel, foil (not shown), and the foils are preferably then electron-beam welded in circles surrounding each source spot 22 (as indicated by the dashed lines 16$a$ in FIG. 3) so as to isolate each source spot 22. This procedure of manufacture of positron assembly 20 will provide a multi-spot, sealed positron source.

The number of source spots 22 is preferably equal to the number of scintillator detectors 16; additionally, it is preferred that the distribution of these source spots 22 on the positron source assembly match with the distribution of BaF$_2$ scintillators 16, such that each scintillator 16 will be "looking" directly on a spot 22 during testing. In FIG. 3, source spots 22 are shown within dashed circles 16$a$, which correspond to locations of the scintillators 16 within detector assembly 10.

The present invention also contemplates a method of nondestructively testing semiconductor wafers using the apparatus of the present invention. In a preferred method of testing, multi-spot positron source 20 is sandwiched between two subject wafers 30, as shown in FIG. 1. This assembly is then placed in between two multi-detector assemblies 10. The orientation of each multi-detector assembly 10 must be aligned with respect to the source assembly so that a pair of opposing scintillator detectors 16 (comprising one detector 16 from each multi-detector assembly 10) "looks" directly on a source spot 22 that is in the middle of a line joining the two detectors 16 of this pair. This arrangement will help to ensure that each source spot 22 is "viewed" directly by the pair of scintillator detectors 16.

Coupled to each scintillator detector is photomultiplier 18, which generates anode output pulses in response to energy loss in the scintillator by emission of gamma rays from the source spot on the test wafer 30. Each scintillator detector 16 may be coupled to a photomultiplier tube 18 remotely by way of suitable fiber optics (not shown). This would increase the number of spots that could be measured simultaneously on a target material. These output pulses from photomultipliers 18 are fed into Fast Constant Fraction Differential Discriminator arrays 40 and 41, comprising, for example, EG&G Ortec model 583 Constant Fraction Differential Discriminators.

As shown in FIG. 1, by way of example only, discriminator array 40 is configured to measure the emission of the "start" or 1.28 MeV gamma ray. Discriminator array 41 is configured to measure the emission of the "stop," or 0.51 MeV gamma ray. The outputs from these discriminators are routed through START and STOP channels 42 and 44, respectively, of a specially designed set of Time-to-Amplitude Converters (TAC) 50, such as EG&G Ortec model 437A Time-To-Amplitude Converters, which can process all of the respective start and stop signals simultaneously.

TAC 50 delivers an output pulse having an amplitude proportional to the time interval between the birth and annihilation of the positron. The pulse height output from each pair of the START and STOP channels is then routed through channels 52 to different memory segments of multichannel analyzer 60, such as a Norland 5400 Multichannel Analyzer, which sorts the pulses in accordance with their amplitudes. Multichannel analyzer 60 has multiple storage channels, each corresponding to a particular time interval, to permit the accumulation of counts corresponding to various delay times encountered. Data from multichannel analyzer 60 may be fed through channels 62 to a computing means, such as computer 70, for the storage and analysis of the data.

In this manner, a positron-lifetime spectrum is collected from each spot 22 of positron source 20 that, in turn, "looks" at a given area on wafer 30. Computer 70 keeps track of the location of each source spot 22 and the corresponding lifetime spectrum originating from that spot. By using a large number of scintillator detectors 16 viewing the wafer 30 under study, a corresponding large number of positron lifetime spectra may be collected simultaneously in a period of about 30 minutes.

Once the data points have been collected, each lifetime spectrum may be analyzed for a mean positron lifetime by computer 70. Computer 70 will be given a relationship between the mean positron lifetime and vacancy concentration. The vacancy concentrations, derived from the lifetime results, may then be plotted on, for example, a computer screen, as a function of location on the wafer. Thus, the user may view on the screen changes in vacancy contents across an entire wafer. From a knowledge of the acceptable levels of these defects, a decision may be made whether the test wafer 30, or any portion thereof, should be used for device fabrication.

If additional details are needed, the stored lifetime spectra may be analyzed for several lifetime components. In that case, the computer memory will contain a given resolution function that may be used to deconvolute the lifetime spectra in order to obtain additional details. These details will permit information about, for example, the concentrations of monovacancies vs. divacancies.

The computer program most commonly used to analyze positron lifetime spectra (PATFIT) is commercially available from CPC Program Library, Queen's University of Belfast, N. Ireland. The reference to this program is P. Kirkegaard, M. Eldrup, O. E. Mogensen, and N. J. Pedersen, Computer Physics Communications, 23 307–335 (1981). A version of this program suitable for a personal computer is also available from the CPC Program Library.

Figure 4:
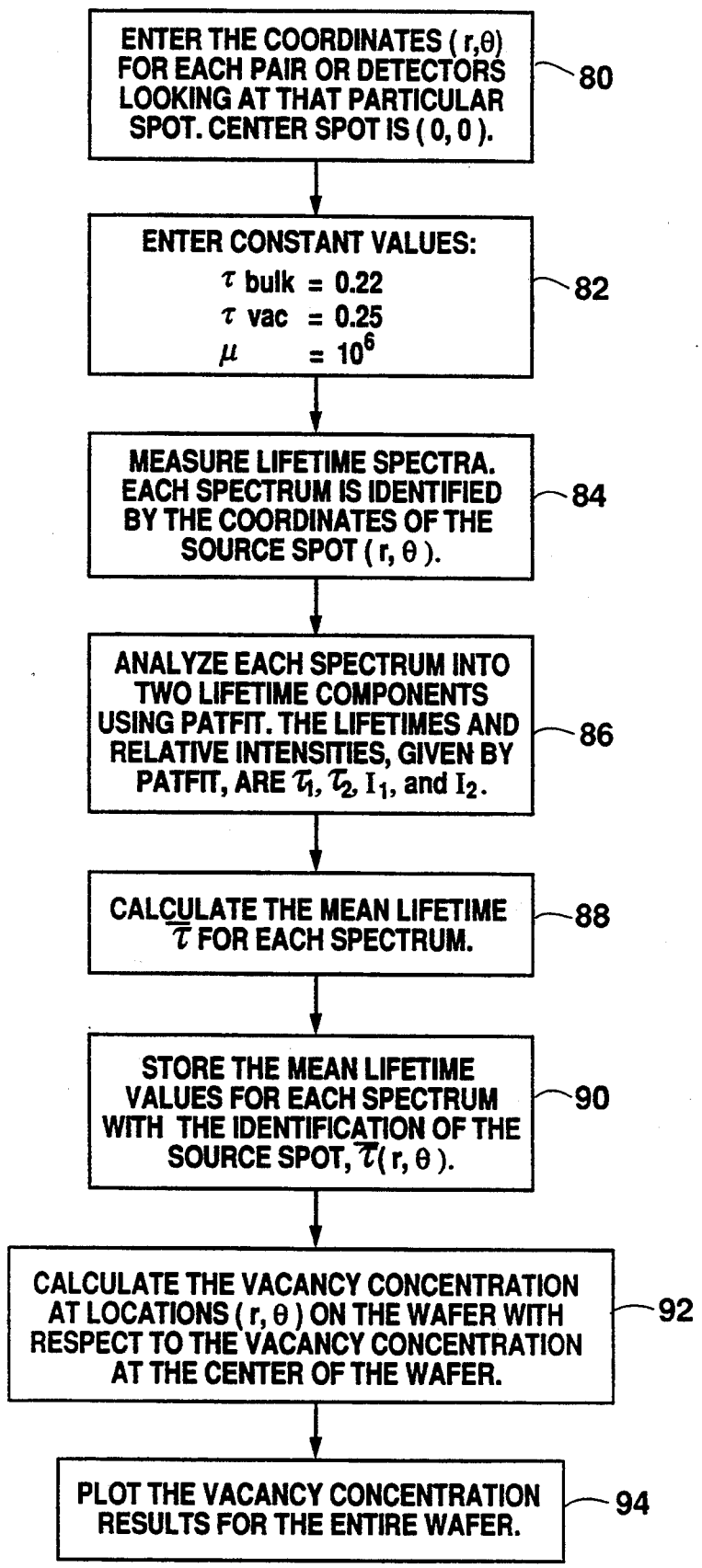
FIG. 4 is a flow chart illustrating computations performed by the testing system of FIG. 1.

For industrial quality control applications, where a rapid and qualitative analysis for the relative concentration of vacancies is more desirable than a detailed quantitative analysis, a suggested procedure is outlined in FIG. 4. To set up the computations, the coordinates (given by the radius r and angle of rotation $\Theta$) for each pair of opposing detectors looking at a particular spot are entered (80). The center spot of the sample is denoted (0,0). The vacancy concentration at location (r,$\Theta$) on the sample wafer with respect to the vacancy concentration at the center of the wafer is given by the formula:

$$\frac{C_v(r, \Theta)}{C_v(0, 0)} = \frac{(\tau(r, \Theta) - \tau_{bulk})}{(\tau_{vac} - \overline{\tau}(r, \Theta))} \cdot \frac{(\overline{\tau}_{vac} - \tau(0, 0))}{(\overline{\tau}(0, 0) - \tau_{bulk})} \quad (1)$$

where the constant values $\tau_{bulk}$ and $\tau_{vac}$ are 0.22 and 0.25, respectively (82). The value of $\mu$ (the positron trapping rate per unit concentration of vacancies) is $10^6$.

Next, the system disclosed herein is used to measure the lifetime spectrum for each source spot, wherein each spectrum is identified by the coordinates (r,$\Theta$) of each source spot (84). The individual spectra are then analyzed into two lifetime components (86). The computer program PATFIT may be used for this analysis. The lifetimes ($\tau$) and relative intensities (I) of these two components are given by PATFIT as $\tau_1$, $\tau_2$, $I_1$, and $I_2$ (86).

The mean lifetime $\overline{\tau}$ is then calculated (88) by using the following formula for each spectrum:

$$\overline{\tau} = \frac{(I_1 \tau_1 + I_2 \tau_2)}{(I_1 + I_2)} \quad (2)$$

The mean lifetime values for each spectrum are then stored with the identification of the source spot, $\tau(r,\Theta)$ (90). Finally, the vacancy concentration at each location (r,$\Theta$) across the wafer with respect to the vacancy concentration at the center of the wafer is computed using formula (1) (92). These results may then be plotted using conventional plotting devices, or may be displayed on a computer monitor using commercially available plotting programs (94).

The absolute concentration of vacancies at any point (r,$\Theta$) on the wafer may be calculated from:

$$C_v(r, \Theta) = \frac{(\overline{\tau}(r, \Theta) - \tau_{bulk})}{\mu \tau_{bulk}(\tau_{vac} - \overline{\tau}(r, \Theta))} \quad (3)$$

Thus, the method and apparatus of the present invention comprise a versatile tool for the rapid and nondestructive quality control of defects in wafers in the semiconductor industry.

The data collection and processing may also be accomplished by using CAMAC electronics in a manner known to those of skill in the art.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. A method of nondestructively determining the existence and location of lattice defects substantially simultaneously for a plurality of areas in a semiconductor material, comprising:

substantially simultaneously subjecting a plurality of areas of said semiconductor material to positron radiation;

utilizing a plurality of radiation detectors to separately and substantially simultaneously detect the times of application of positron radiation to each said area and the times of emission from each said area of characteristic energy produced upon annihilation of the positrons introduced into each said area;

determining delays between the times of application of said positron radiation to each said area and the times of emission of said characteristic energy from each said area resulting from said annihilation; and obtaining an indication of the lifetimes of said positrons within each said area utilizing said delays, said lifetimes correlating to lattice defects within each said area of said semiconductor material.

2. The method of claim 1, further comprising:

determining lattice defects as a function of location on said semiconductor material utilizing said indication of the lifetimes of said positrons within each said area.

3. The method of claim 2, further comprising:

visually indicating the lattice defects for a plurality of said areas of said semiconductor material.

4. A method of nondestructively determining substantially simultaneously the existence and location of lattice defects in substantially all of a semiconductor wafer, comprising:

substantially simultaneously subjecting substantially an entire semiconductor wafer to positron radiation;

sensing a timing of the application of each positron to each of a plurality of areas of said semiconductor wafer substantially simultaneously, said plurality of areas covering substantially all of said semiconductor wafer;

detecting an emission from each said area substantially simultaneously of characteristic energy produced upon annihilation of each positron introduced into said areas;

determining a delay between the time of application of each positron to each said area and the time of emission of said energy resulting from its annihilation to determine the lifetimes of the positrons introduced into the wafer at each of said areas; and determining the existence of lattice defects as a function of location in substantially all of said semiconductor wafer utilizing said lifetimes.

5. The method of claim 4, further comprising the step of:

visually indicating lattice defects as a function of location for substantially all of said semiconductor wafer.

6. An apparatus for nondestructively determining the existence of lattice defects substantially simultaneously for a plurality of areas in a semiconductor material, comprising:

a plurality of sources of positron radiation for directing positrons into a corresponding plurality of areas of said semiconductor material substantially simultaneously;

a corresponding plurality of radiation detectors for sensing the application of positrons to each said area and the characteristic energy associated with annihilation of the positrons introduced into each said area substantially simultaneously; and sensing means for measuring a time interval between the time of application of positrons to each said area and the annihilation of the positrons in each said area, to determine substantially simultaneously for each said area the lifetimes of the positrons introduced into said area, said lifetimes correlating to lattice defects in each said area.

7. The apparatus of claim 6, further comprising:

visual display means coupled to said sensing means for indicating accumulated positron lifetime data for all areas of said semiconductor wafer.

8. An apparatus for determining lattice defects as a function of location substantially simultaneously for substantially all of a semiconductor wafer, comprising:

a plurality of sources of positron radiation arranged on one side of the wafer to simultaneously expose a corresponding plurality of adjoining areal portions of the wafer;

a separate pair of opposing radiation detectors aligned with each said source and each said corresponding areal portion of the wafer, said plurality of radiation detectors operable to substantially simultaneously detect application of positrons to each said corresponding areal portion of the wafer and radiation resulting from annihilation of the positrons within each said corresponding areal portion of the wafer; and sensing means operable to compare the times of detection by the radiation detectors of the application of positrons and the radiation resulting from said annihilations to obtain positron lifetimes within each said corresponding areal portion of the wafer, said lifetimes correlating to lattice defects.

9. The apparatus of claim 8, wherein said plurality of sources of positron radiation is a multi-spot positron assembly, comprising:

a plurality of source spots of positron emitting material coupled between two pin-hole free foils.

10. The apparatus of claim 9, wherein said foils are electron-beam welded around each source spot and wherein said source spots are arranged in a plurality of circles.

11. A method of nondestructively determining the existence and location of lattice defects substantially simultaneously in a plurality of corresponding areas of two semiconductor wafers, comprising:

positioning a semiconductor wafer on each side of a multi-spot positron radiation source, said semiconductor wafers being substantially parallel;

aligning a pair of opposing radiation detectors with each source spot of said multi-spot positron radiation source, each said pair of opposing radiation detectors being directed to a pair of aligned areas from said semiconductor wafers;

utilizing said multi-spot positron radiation source to apply positron radiation substantially simultaneously to each said pair of aligned areas;

utilizing each said pair of opposing radiation detectors to detect substantially simultaneously the application of positron radiation to each said pair of aligned areas and the emission of characteristic energy produced upon annihilation of the positrons introduced into each said pair of aligned areas;

determining delays between the times of application of said positron radiation to each said pair of aligned areas and the times of emission of said characteristic energy from each said pair of aligned areas; and utilizing said delays to determine substantially simultaneously the lifetimes of said positrons within each said pair of aligned areas, said lifetimes correlating to lattice defects in each said pair of aligned areas of said semiconductor wafers.

12. The method of claim 11, further comprising:

determining lattice defects within each of said plurality of said pairs of aligned areas of said semiconductor wafers; and visually indicating said lattice defects for said plurality of said pairs of aligned areas of said semiconductor wafers.

13. An apparatus for nondestructively determining the existence and location of lattice defects substantially simultaneously in a plurality of corresponding areas of two semiconductor wafers, comprising:

a multi-spot positron radiation source adapted to be sandwiched between said two semiconductor wafers;

a pair of opposing radiation detectors aligned with each source spot of said multi-spot positron radiation source and directed in operation to a pair of aligned areas on said semiconductor wafers, said plurality of pairs of opposing radiation detectors for sensing substantially simultaneously for each said pair of aligned areas the times of application of said positron radiation to each said pair of aligned areas and the times of emission of said characteristic energy from each said pair of aligned areas;

a sensing means coupled to said plurality of pairs of opposing radiation detectors for determining substantially simultaneously lifetimes for positrons within each of said pair of aligned areas, said lifetimes correlating to lattice defects in each said pair of aligned areas.

14. The apparatus of claim 13, further comprising:

a display means for visually displaying an indication of lattice defects in each said pair of aligned areas of said semiconductor wafers.

15. The apparatus of claim 13, wherein said multi-spot positron radiation source, comprises:

a plurality of source spots of positron emitting material coupled between two pin-hole free foils.

16. The apparatus of claim 15, wherein said foils are electron-beam welded around each source spot and wherein said source spots are arranged in a plurality of circles.

* * * * *